United States Patent
Lin et al.

[11] Patent Number: 5,868,667
[45] Date of Patent: Feb. 9, 1999

[54] PRESSURE-EQUALIZING CAP

[75] Inventors: Szu-Min Lin, Laguna Hills; Paul Taylor Jacobs, Trabuco Canyon; Henry Ka-Wah Hui, Laguna Niguel; Les Authur Feldman, Calabasas Hills, all of Calif.

[73] Assignee: Ethicon, Inc., Irvine, Calif.

[21] Appl. No.: 49,507

[22] Filed: Mar. 27, 1998

[51] Int. Cl.$^6$ ........................................... A61B 1/00
[52] U.S. Cl. ........................................ 600/133; 600/121
[58] Field of Search .................................. 600/133, 121, 600/122, 123, 124, 125, 127

[56] References Cited

U.S. PATENT DOCUMENTS

| | | |
|---|---|---|
| 4,241,729 | 12/1980 | Aoshiro . |
| 4,545,369 | 10/1985 | Sato . |
| 4,750,477 | 6/1988 | Wardle . |
| 4,878,484 | 11/1989 | Miyagi ...................................... 600/133 |
| 4,943,414 | 7/1990 | Jacobs et al. . |
| 5,154,166 | 10/1992 | Chikama . |
| 5,188,094 | 2/1993 | Adair ...................................... 600/133 |
| 5,201,908 | 4/1993 | Jones ...................................... 600/125 |
| 5,313,934 | 5/1994 | Wiita et al. ............................. 600/133 |
| 5,349,941 | 9/1994 | Hori . |
| 5,415,157 | 5/1995 | Welcome . |
| 5,419,310 | 5/1995 | Frassica et al. . |
| 5,447,148 | 9/1995 | Oneda et al. . |
| 5,474,089 | 12/1995 | Waynant . |
| 5,545,150 | 8/1996 | Danks et al. . |
| 5,547,456 | 8/1996 | Strobl et al. . |
| 5,575,756 | 11/1996 | Karasawa et al. . |
| 5,580,530 | 12/1996 | Kowatsch et al. . |
| 5,599,278 | 2/1997 | Habbard ................................ 600/133 |
| 5,630,782 | 5/1997 | Adair . |
| 5,634,880 | 6/1997 | Feldman et al. . |
| 5,634,881 | 6/1997 | Francis .................................. 600/133 |
| 5,643,175 | 7/1997 | Adair . |
| 5,676,682 | 10/1997 | Yoon . |

FOREIGN PATENT DOCUMENTS

| | | |
|---|---|---|
| 5220110 | 8/1993 | Japan ................................... 600/133 |
| 5-253168 | 10/1993 | Japan . |

*Primary Examiner*—Paul J. Hirsch
*Attorney, Agent, or Firm*—Knobbe, Martens, Olson & Bear, LLP

[57] ABSTRACT

A device for use with an endoscope is provided. The device allows the equalization of the pressure between an internal space of the endoscope and an environment outside the endoscope. The device includes a housing defining an opening, a gas-transmissive removal zone in the opening and at least one hydrophobic breathable membrane between the gas-transmissive removal zone and the environment. The housing of the device is adapted to receive a port that is connected to an internal space of the endoscope. The gas-transmissive removal zone includes a desiccant material and a material which removes an antimicrobial agent.

30 Claims, 7 Drawing Sheets

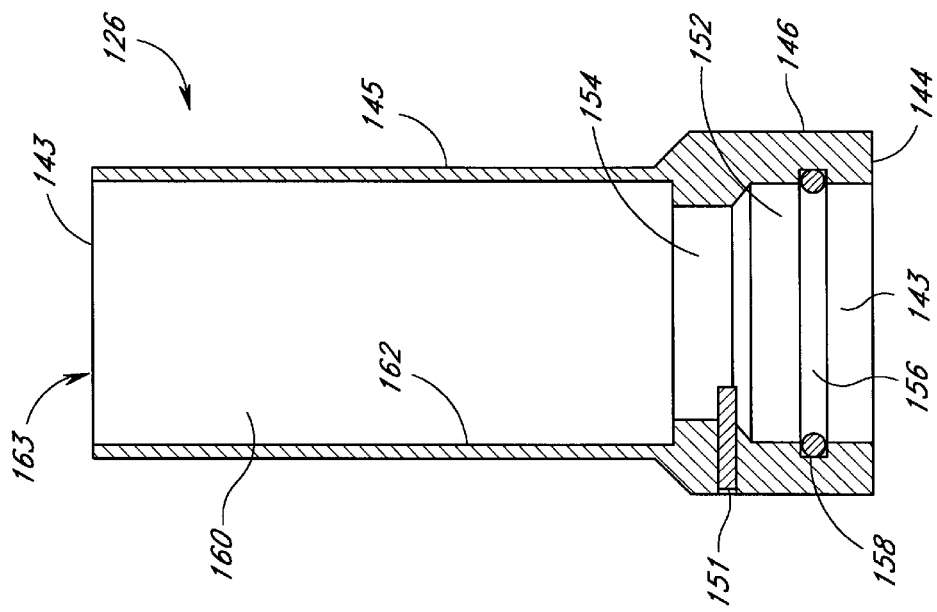
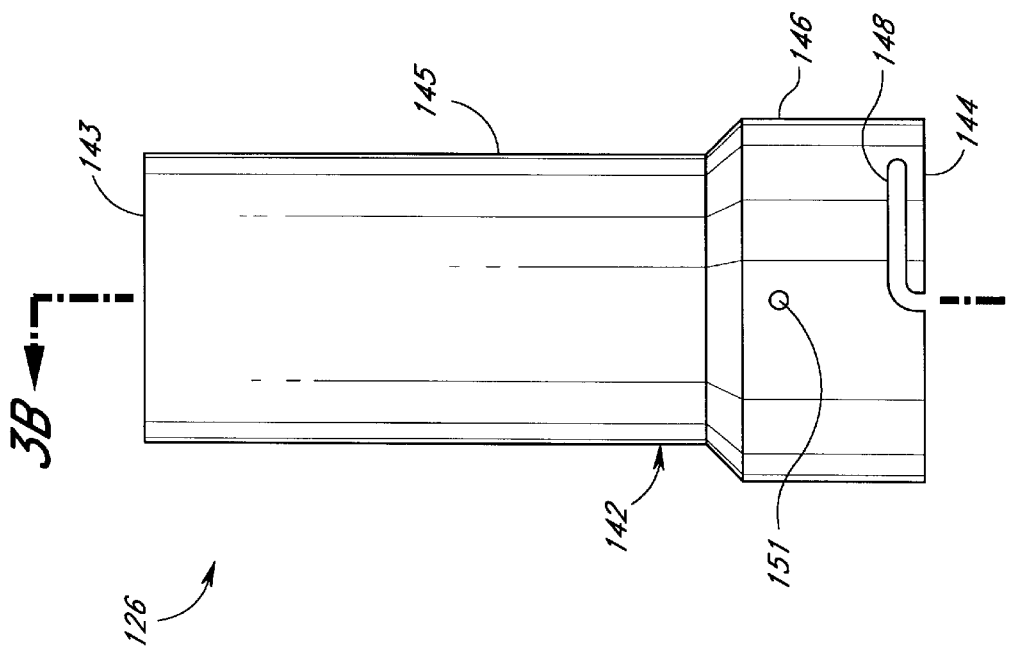
FIG.3B
FIG.3A

PRESSURE-EQUALIZING CAP

BACKGROUND OF THE INVENTION

1. Field of the Invention

This invention generally relates to a device and a method for equalizing pressure between an internal space in an endoscope and an environment about the endoscope.

2. Description of the Related Art

In modern medical practices, it has been a common practice to sterilize instruments used for medical or surgical purposes before each use. It is important that the sterilization and cleaning of such instruments be performed efficiently and quickly without damaging the materials or functionality of the device. However, the ever increasing complexity of such instruments requires corresponding modifications in conventional cleaning and sterilization equipment and processes, which makes the sterilization and cleaning related problems one of the critical aspects of using such instruments.

This is particularly relevant to instruments comprising elongated channels, such as endoscopes. A typical endoscope generally includes two elongated tubular bodies having a distal portion and a proximal portion. The distal portion of the endoscope is generally flexible enough to be inserted into a human body or animal body, and is often referred to in the art as an insertion tube. The endoscope usually contains various internal components, such as wires, for controlling movements of the endoscope as well as a number of tubular passages for passing air, liquid or instruments. In addition, endoscopes are furnished with an image transmission means, such as fiber optic cables, or CCD camera with electrical cables, to transmit images from a distal location in a body.

Such components are conveniently sealed and protected in an internal space of the endoscope by a gas and liquid tight sheath. This sheath is generally made of an elastomeric material and surrounds the endoscope. After each use, it is important that the interior surface of the tubular passages, along with the surrounding sheath, be carefully cleaned and sterilized for reasons of sanitation. At present, some conventional sterilization processes utilize sterilant gas, such as hydrogen peroxide or ethylene oxide, in low pressure sterilization chambers to sterilize endoscopes. However, in such sterilization processes, as the pressure is lowered, the air trapped at the internal space of the endoscope exerts pressure against the elastomeric sheath. If this pressure at the internal space is not properly released, the elastomeric sheath may rupture with the high pressure. In fact, typical prior art endoscopes use a sealable port for releasing the entrapped air during any reduced pressure sterilization process. During a sterilization process in a reduced pressure environment, a cap sealing this sealable port may be opened to allow the internal space of the endoscope to communicate with the sterilizing atmosphere so that the excess pressure within the endoscope may be relieved. However, this port needs to be closed during the washing procedures of the exterior of the endoscope to prevent the flow of cleaning liquid into the endoscope. Therefore, an operator has to either close or open the sealing cap, depending on the type of treatment.

Unfortunately, this situation presents a special challenge for newer in-situ sterilization processes which use liquid sterilant at atmospheric pressure and vapor sterilants in reduced pressure in a continuous cycle. In such systems, briefly, a liquid sterilant, such as liquid hydrogen peroxide, is initially delivered to a sterilization chamber containing articles to be sterilized so that these articles can be pretreated with the liquid sterilant. Subsequently, the liquid sterilant is vaporized in the chamber using vacuum so that the articles are exposed to the sterilant vapor. It will be appreciated, however, that it is very difficult to design a mechanical system which can sequentially close and open this port in the chamber as the sterilization cycle advances from the liquid treatment stage to the reduced pressure vapor sterilization stage.

Therefore, there is a need for alternative systems which allow cleaning and sterilization of endoscopes in the sterilization processes using liquid and vapor sterilants in a continuous cycle in a sterilization chamber.

SUMMARY OF THE INVENTION

The aforementioned needs are satisfied with the apparatus and the process of the present invention. Specifically, the vent cap of the present invention allows the pressure to equalize between the internal space of the endoscope and the environment surrounding the endoscope's sheath, while reducing the flow of any liquid, water vapor and hydrogen peroxide into the endoscope's internal space. One embodiment of the present invention utilizes a non-breathable membrane to block the fluid communication between the internal space of the endoscope and the environment surrounding the endoscope. However, as the pressure of the environment is reduced, the non-breathable membrane breaks open thereby equalizing the pressure between the internal space of the endoscope and the environment surrounding the endoscope.

It will be appreciated that there are multiple aspects of the present invention. In one aspect of the present invention, a device for use with an endoscope, that allows the equalization of the pressure between an internal space of the endoscope and an environment outside the endoscope, is provided. The device includes a housing defining an opening, a gas-transmissive removal zone in the opening and at least one hydrophobic breathable membrane between the gas-transmissive removal zone and the environment. The housing of the device is adapted to receive a port that is connected to an internal space of the endoscope. The gas-transmissive removal zone includes a desiccant material and a material which removes an antimicrobial agent.

In another aspect of the present invention, a method for equalizing pressure within an internal space of an endoscope with a pressure in an environment outside the endoscope is provided. The endoscope has a port that is connected to the internal space. The method includes the steps of placing the endoscope within a chamber, connecting a pressure control device to the port, subjecting the endoscope to a liquid phase environment at a first pressure and subjecting the endoscope to a subsequent gas phase environment including water vapor and gaseous antimicrobial agent at a second pressure less than the first pressure. However, the placing and connecting steps can be performed in either order. The pressure control device has a housing that defines an opening and a gas-transmissive removal zone positioned within the opening. Further, in the step of subjecting the endoscope to a liquid phase environment at a first pressure, the removal zone reduces entry of the liquid into the internal space of the endoscope through the opening. Moreover, in the step of subjecting the endoscope to a subsequent gas phase environment including water vapor and gaseous antimicrobial agent at a second pressure less than the first pressure, a phase change of at least some of liquid to a gas is induced. The removal zone absorbs the water vapor and removes the antimicrobial agent and permits at least some air within the internal space of the endoscope to escape to the environment through the opening.

In another aspect of the invention, a device for use with an endoscope that allows the equalization of the pressure between an internal space of the endoscope and an environment is provided. The device includes a housing defining an opening, a membrane sealing the opening and a sharp-edged device adapted to puncture the membrane. The housing of the device is adapted to receive the port that is connected to an internal space of the endoscope. The membrane is gas and liquid impermeable and breaks when a reduced pressure is applied. Further, the sharp-edged device is adapted to puncture the membrane when the reduced pressure is applied.

In yet another aspect of the invention, a method for equalizing pressure within an internal space of an endoscope with a pressure in an environment outside the endoscope is provided. The endoscope has a port that is connected to the internal space. The method includes the steps of placing the endoscope within a chamber, connecting an adaptor to the port, subjecting the endoscope to a liquid at a first pressure and subjecting the endoscope to a subsequent gas phase environment at a second pressure lower than the first pressure. However, the placing and the connecting steps can be performed in either order. The adaptor has a housing that defines an opening, and a non-permeable membrane seals the opening. In the step of subjecting the endoscope to a liquid at a first pressure, the membrane prevents transmission of gas and liquid between the internal space of the endoscope and the environment outside the endoscope through the opening. Further, in the step of subjecting the endoscope to a subsequent gas phase environment, the membrane breaks upon application of the reduced pressure and permits gas within the internal space of the endoscope to escape to the environment through opening.

Hence, the present invention allows both atmospheric pressure liquid phase cleaning and/or sterilization and subsequent reduced pressure drying and/or sterilization of endoscopes in a continuous fashion.

These and other objects and advantages of the present invention will become more fully apparent from the following description taken in conjunction with the accompanying drawings.

BRIEF DESCRIPTION OF THE DRAWINGS

FIG. 3A is a perspective view of a vent cap of the present invention;

FIG. 3B is a partial sectional view of the vent cap taken along the lines 3B—3B of FIG. 3A;

DETAILED DESCRIPTION OF THE PREFERRED EMBODIMENT

Figure 1:
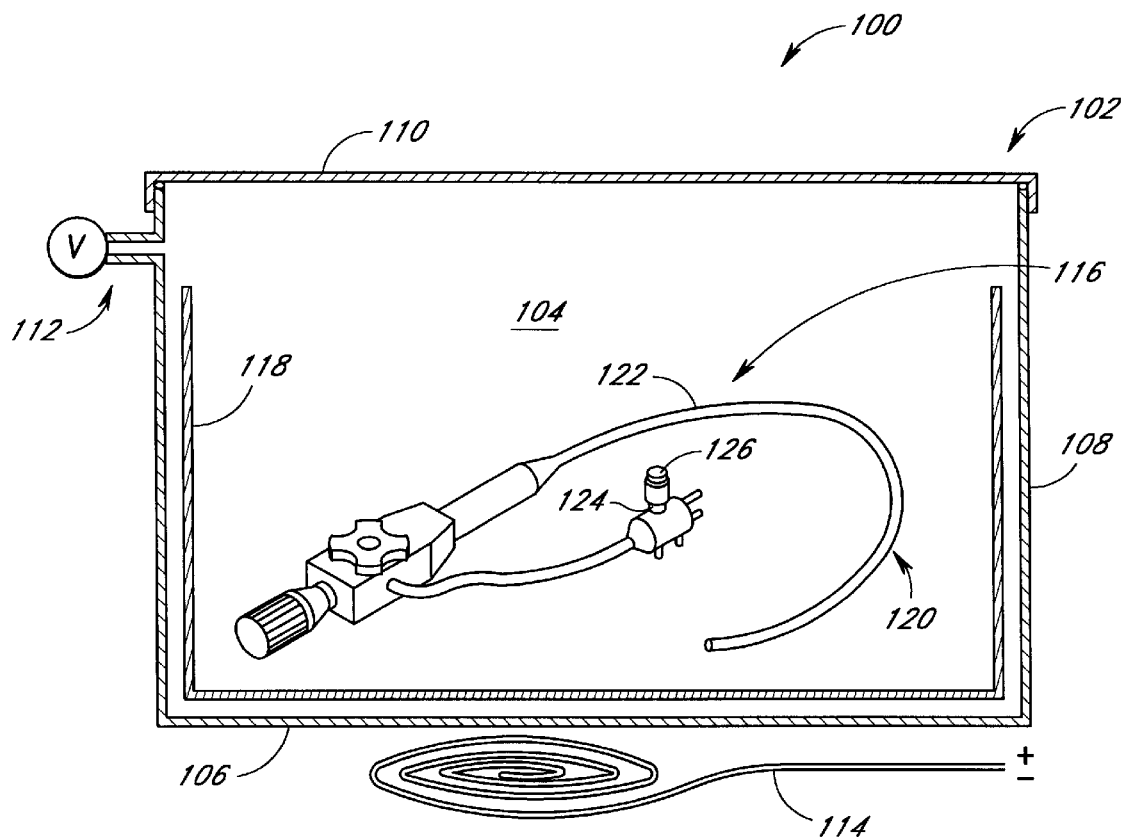
FIG. 1 is a schematic view of a sterilization system comprising an endoscope.

As will be described hereinbelow, the present invention allows the pressure to equalize between the internal space of an endoscope and the environment outside the endoscope's sheath, while reducing the flow of any liquid, water vapor and hydrogen peroxide into the endoscope's internal space. Reference will now be made to the drawings wherein like numerals refer to like parts throughout. FIG. 1 shows a cleaning and/or sterilization system 100 for sterilization and cleaning of lumen devices, such as endoscopes. The system 100 comprises a cleaning and/or sterilization chamber 102 having an inner chamber 104 for containment of the articles being sterilized. The inner chamber 104 is defined by a chamber floor 106, a peripheral wall 108 and a sealable lid 110. A valve 112 on the peripheral wall 108 may connect the inner chamber 104 to a vacuum pump (not shown). The chamber 102 may also be furnished with a heating device 114, such as a resistance heater, to provide heat for the inner chamber 104 when it is necessary. The sterilant to be utilized in the present invention is preferably a hydrogen peroxide (peroxide) solution which is positioned within the chamber 102 and evaporates when a vacuum is applied to the chamber 102.

As is also shown in FIG. 1, an exemplary endoscope device, preferably a flexible endoscope device, 116 may be placed into the chamber 102 in an optional sterilization tray 118. The endoscope 116 comprises a flexible portion 120 for insertion into a patient's body with the flexible portion 120 being encased within an elastomeric sheath 122. A port 124 opens to an internal space (not shown) of the endoscope 116 and allows pressure communication between the internal space and the environment about the endoseope, which, in this case, is the inner chamber 104 in the sterilization system 100. As will be explained more fully below, in this embodiment, a vent cap 126, according to the present invention, may be attached to the port 124 as in the manner shown in FIG. 1.

Figure 2:
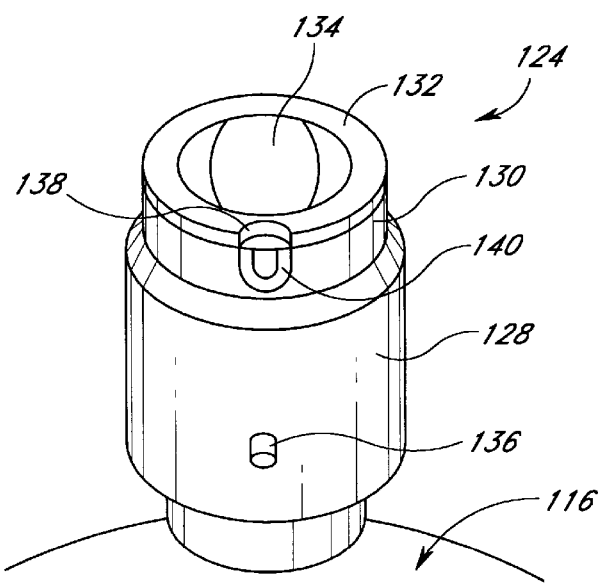
FIG. 2 is a perspective view of a pressure port of the endoscope shown in FIG. 1.

As illustrated in FIG. 2, the port 124 comprises a cylindrical body 128 projecting outwardly from the endoscope 116. An annular rotatable collar 130 is received within the port body 128 and an annular cover plate 132 is disposed above the collar 130 so as to be rigidly connected to the body 128. Rotation of the collar 130 operates a valve member 134 to selectively open and close the internal space of the endoscope 116 to the environment around the endoscope 116 via the port 124. A guide pin 136 projects radially outwardly from the port body 128 and a notch 138 on the cover plate 132 aligns with a notch 140 on the collar 130. As will be explained more fully hereinbelow, this application incorporates check valves, a catalyst, an endoscope port and an attachment portion of the vent cap that is engaged with the port when the vent cap is attached to the endoscope. These are similar to the check valves, the catalyst, the endoscope port, and the attachment portion of the vent cap which are all disclosed in U.S. Pat. No. 5,634,880 to Feldman et al. and incorporated herein by reference in its entirety.

The port 124 may be adapted to receive the vent cap 126 according to the present invention. As will be described more fully below in FIGS. 3A–3B, the vent cap 126 has a track 148 for receiving the guide pin 136 and an engagement pin 151 for engaging the collar notch 140. When the cap 126 is placed onto the port 124 and rotated, the valve member 134 opens to place the interior of the endoscope 116 into pressure communication with the inner chamber 104 of the sterilization system 100 through a hole in the cap 126.

FIG. 3A illustrates the vent cap 126. The cap 126 may be comprised of a generally cylindrical body 142 having a first end 143 and a second end 144. The cylindrical body 142 may be comprised of a first portion 145 and a second portion 146 which has a channel 148 therein for receiving the guide pin 136 on the port 124 (See FIG. 2). The first and second portions 145 and 146 may be formed as one piece, or formed separately and scalably connected using well known techniques in the art. The body 142 of the cap 126 may be made of a metal, such as stainless steel or aluminum, or a plastic, such as PE (polyethylene) or PP (polypropylene). The channel 148 may extend axially into the second portion 146 a short distance from the second end 144 from where the channel 148 extends circumferentially approximately one quarter of the circumference of the second portion 146. Accordingly, the cap 126 may be placed over the port 124, with the pin 136 of the port 124 received within the channel 148, and the cap 126 then rotated one quarter turn as the guide pin 136 travels along the channel 148. An engagement pin 151 extends radially inwardly from the second portion 146 of the body 142 and engages the collar notch 140 when the guide pin 136 is received within the channel 148. As the cap 126 is rotated, the engagement pin 151 rotates the collar 130 to open the valve member 134.

FIG. 3B shows the interior structure of the second portion 146 of the cap body 142 and discloses a lower housing 143 having a first axial bore 152 and a second axial bore 154. The first axial bore 152 extends into the second portion 146 of the body 142 from the second end 144 and is sized to receive the port body 128 (See FIG. 2). The first axial bore 152 extends somewhat further into the second portion 146 and has a smaller diameter so as to receive the port collar 130 and cover plate 132. An annular groove 156 in the second portion 146 of the body 142 and located at the first bore 152 receives an o-ring 158 to seal the cap 126 to the port 124.

As shown in FIG. 3B, the first portion 145 of the body 142 comprises a third axial bore 160 which is defined by an inner wall 162. The third axial bore may extend from the lower housing 143 to an opening 163 at the first end of the cap 126. For the purpose of clarity, the third axial bore 160 will be referred to as the cap housing hereafter. The first portion 145 may be comprised of a single piece or a combination of various pieces. As will be explained more fully in the following embodiments, the cap housing 160 may receive one or more components which allow the exchange of gas between the internal space of the endoscope 116 and the inner chamber 104, but reduce the flow of any liquid and water vapor into the endoscope 116.

Figure 4:
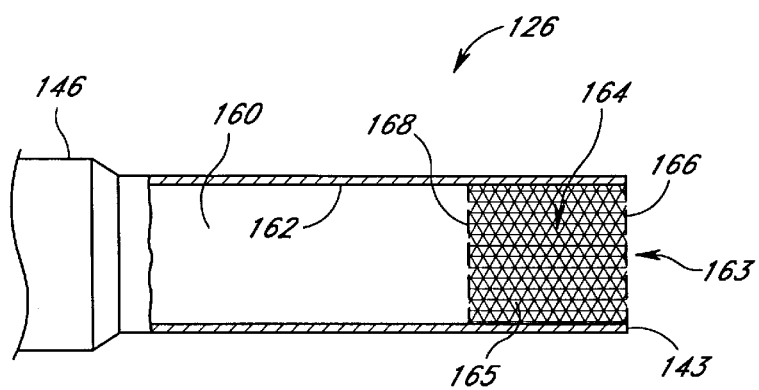
FIG. 4 is a schematic view of a first embodiment of the vent cap wherein the vent cap includes a first control member.

FIG. 4 shows, in side view, a preferred embodiment of the cap housing 160 of the vent cap 126. In this embodiment, a first pressure control member 164 may be disposed within the housing 160. The first pressure control member 164 may preferably be comprised of a gas transmissive removal zone 165 which is sealably sandwiched between a first and second membrane 166 and 168 and surrounded by a portion of the inner wall 162 of the housing 160. The first pressure control member 164 may preferably be located adjacent to the first end 143 of the cap 126. In this respect, the first membrane 166 is sealably attached to the circumference of the opening 163 while the second membrane is again sealably circumferentially attached (e.g., thermally melted, ultrasonically melted, glued or attached in other ways known in the art) to the inner wall of the housing 160 as in the manner shown in FIG. 4.

In the preferred embodiment, the membranes 166 and 168 may be made of any hydrophobic breathable barrier (i.e., breathable membrane) which is permeable to gas. Typical breathable membranes that may be used for this purpose include porous PTFE, such as Gor-Tex™, or porous polyolefin, such as Tyvek™ or non-woven polypropylene. In this embodiment, however, the second membrane 168 may alternatively be made of a gas transmissive membrane such as paper-filter or glass-filter, or the like. Preferably, the gas transmissive removal zone 165 is comprised of a mixture of a moisture absorber, i.e., a desiccant material, and a material for removing antimicrobial agents such as hydrogen peroxide or ethylene oxide. If the antimicrobial agent is hydrogen peroxide, a catalyst may be used to decompose the hydrogen peroxide into water and oxygen. However, if the antimicrobial agent is ethylene oxide, an ethylene oxide absorbing material may be used to absorb ethylene oxide. Accordingly, ethylene oxide may be absorbed by activated charcoal or a molecular sieve such as zeolite. Examples of common chemicals used as the moisture absorber may include, but may not be limited to drying agents such as $P_2O_5$, BaO, CaO or $Al_2O_3$ and possible combinations thereof. In this respect, a preferred catalyst material for hydrogen peroxide may be a metallic wool, such as those made of copper or copper alloys which are capable of decomposing hydrogen peroxide into water and oxygen. Other materials such as palladium, platinum, copper, silver, iron, chromium, manganese, cobalt, nickel, zinc, niobium, molybdenum, rhodium, cadmium, hafnium, tungsten, osmium, iridium, gold, mercury, lead, bismuth, polonium, thorium and their alloys are among other metals which act as a catalyst against hydrogen peroxide.

In the process of the preferred embodiment, to sterilize the endoscope 116 (See FIG. 1) in a low pressure gaseous antimicrobial atmosphere, the vent cap 126 of the preferred embodiment is first placed onto the port 124 of the endoscope 116 as in the manner explained above. As the cap 116 engages with the port 124, the valve member 134 (See FIG. 2) is brought into the open position, thereby placing the internal space of the endoscope 116 into gas communication with the housing 160 of the cap 126. As noted above in the background section, the sterilization cycle may be initiated with a liquid treatment stage so as to pretreat the endoscope 116 using a liquid hydrogen peroxide solution comprising water and hydrogen peroxide. During this stage, the vent cap 126 prevents the flow of this sterilant liquid into the internal space of the endoscope 116. The gas transmissive removal zone 165 of the first pressure member 164 absorbs the water vapor (moisture) and neutralizes any of the hydrogen peroxide vapor which may diffuse through the first breathable membrane 166.

As the pressure is reduced to evaporate the hydrogen peroxide in the chamber 102, the first pressure control member 164 allows air within the internal space of the endoscope 116 to diffuse through the membranes 166 and 168 and the gas transmissive removal zone 165. This, in turn, releases the pressuring air which may otherwise damage the elastomeric sheath 122 of the endoscope 116. Thus, the cap 126 allows the pressure within the internal space of the endoscope 116 to equalize with the pressure in the chamber 102. It is understood that the reduced vacuum process, following the liquid pretreatment stage, results in drying the endoscope by evaporating liquid in the environment. Thus, the reduced pressure process can also be used for vacuum drying. In this embodiment, the liquid pretreatment may, for example, include washing the exterior of the endoscope in a cleaning solution at atmospheric pressure, such as a solution of water and a washing detergent, and subsequently rinsing the endoscope with water. These washing and rinsing steps may be performed in a place which is outside the sterilization chamber 102. The liquid pretreatment may be finalized within the chamber 102 with the liquid sterilization process at atmospheric pressure. Accordingly, in this embodiment, sterilization of the instrument can be achieved before or during the reduced pressure sterilization, either with the liquid sterilant or the sterilant vapor occurring during the reduced pressure process. As the pressure in the endoscope 116 equalizes with the surrounding chamber pressure, the gas transmissive removal zone 165 still absorbs any of the water or neutralizes any of the hydrogen peroxide which may diffuse into the first pressure control member 164.

It should be understood that the use of the vent cap 126 is not limited to the sterilization processes using sterilants in sterilizing environments. Alternatively, the cap 126 may advantageously be used during a cleaning process performed at atmospheric pressure, to clean the endoscope 116, which includes cleaning with a cleaning solution, rinsing with water and then drying under reduced pressure. The cap 126 also advantageously allows the use of integrated sterilization systems which perform the cleaning and sterilization processes in an integrated fashion with a continuous cleaning and sterilization cycle. In such an integrated system, once the cap 126 is attached to endoscope 116, the endoscope 116 is placed into the system so as to be simultaneously cleaned, rinsed, liquid-phase sterilized (all in atmospheric pressure) reduced pressure vapor phase sterilized or vacuum dried in the system.

It is known that if sterilization is performed in connection with electromagnetic radiation to produce a plasma field, the plasma field can be used to enhance the sporicidal activity and to remove the hydrogen peroxide residues. However, in the absence of a plasma field, the hydrogen peroxide is typically removed by vacuum. In any event, once the sterilization is complete, the pressure is raised within the sterilization chamber 102 (See FIG. 1) and the air within the sterilization chamber 102 enters the endoscope 116 through the cap 126. If there is residual hydrogen peroxide or moisture within the sterilization chamber, the gas transmissive removal zone 165 will neutralize the hydrogen peroxide and absorb the moisture before entering the port 124 of the endoscope 116. After the sterilization cycle is complete, the vent cap 126 should be removed from the endoscope 116.

Figures 5A, 5B:
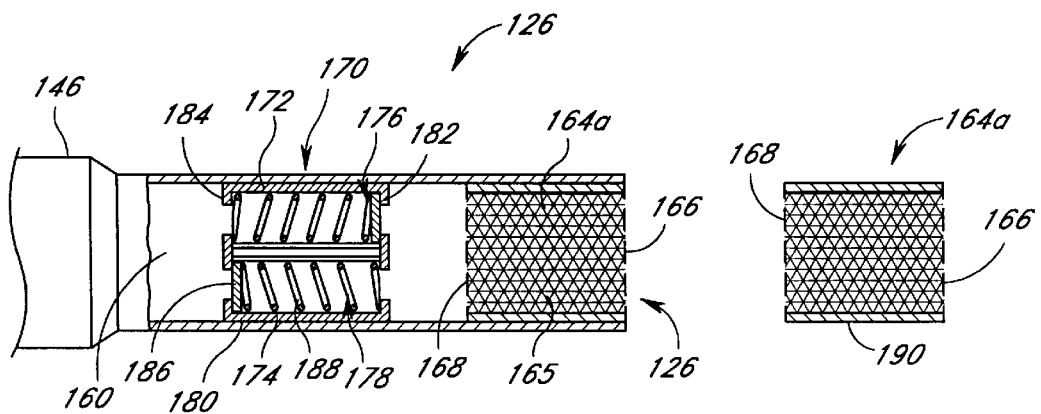
FIG. 5A is a schematic view of a second embodiment of the vent cap wherein the vent cap includes a first and a second control member.
FIG. 5B is a schematic view of a first disposable control member of the vent cap shown in FIG. 5A.

FIG. 5A shows a second embodiment of the vent cap 126 of the present invention. In this embodiment, the housing 160 of the cap 126 comprises a second pressure control member 170 along with a disposable form of the first pressure control member 164 which will be denoted as 164A hereinafter. Further in this embodiment, the second pressure control member 170 may be positioned between the first pressure control member 164A and the lower housing 143 of the second portion 146 as in the manner shown in FIG. 5A. As will be explained more fully below, the disposable first pressure control member 164A in this embodiment may be removably disposed within the housing 160 of the cap 126.

As shown in FIG. 5A, the second pressure control member 170 may be comprised of a dual valve system having an inlet check valve 172 and a outlet check valve 174 which are received respectively by an inlet valve bore 176 and an outlet valve bore 178. The valve bores 176 and 178 are formed in the housing 160 and extend axially into the housing 160 in side-by-side relationship as in the manner shown in FIG. 5A. Both of the inlet and outlet valve bores 176 and 178 are in fluid communication with the internal space of the endoscope 116 and the outside environment through first pressure control member 164A. Each of the inlet and outlet check valves 172 and 174 allow only unidirectional flow, and only in response to a predetermined pressure gradient.

In general, each of the inlet and outlet check valves 172 and 174 comprises a tubular valve body 180 having an interior annular valve seat 182 and a spring seat 184. A valve member 186 is positioned at the downstream of the valve seat 182. A spring 188 extends between the valve seat 182 and the spring seat 184 to bias the valve member 186 against the valve seat 182. When a gas pressure against the valve member 186 overcomes the force of the spring 188, the valve member 186 moves away from the valve seat 182 to allow gas flow through the valve body 180.

The check valves 172 and 174 of the second pressure control member 170 allow the pressure to equalize between the internal space of the endoscope 116 and the environment surrounding the endoscope sheath 122, while preventing free flow of gas into the endoscope 116. The check valves 172 and 174 can advantageously open and close under predetermined pressures and thereby control the pressure in the internal space of the endoscope 116. The springs 188 determine the pressure necessary to open the check valves 172 and 174. Preferably, the spring force should require a pressure differential of 5 to 270 Torr to operate the check valves 172 and 174.

As illustrated in FIG. 5B, in this embodiment, the disposable first pressure control member 164A may be produced as a removable component of the vent cap 126. In this respect, the first pressure control member may, for example, be formed as a container having a cylindrical body 190 filled with a gas transmissive removal zone 165. Either end of the container is sealably covered with breathable membranes 166 and 168. The disposable first member 164A can be sealably disposed along the housing 160 and can be replaced after each sterilization process. This practice, in turn, advantageously saves the relatively expensive cap body 142 and the second pressure control member 170 thereby reducing the overall cost of the sterilization process.

In use, in this embodiment, the first pressure control member 164A functions as in the manner explained above. As for the second pressure control member 170, as the pressure is reduced, the outlet check valve 174 opens to allow air within the endoscope 116 to escape thereby preventing any pressure build up on the elastomeric sheath 122. As the pressure in the endoscope 116 equalizes with the pressure inside the chamber 102, the outlet check valve 174 closes and seals the internal space of the endoscope 116. At the end of the sterilization cycle, the pressure is raised within the sterilization chamber 102. At a predetermined pressure gradient, the inlet check valve 172 of the second pressure control member 170 opens to allow air, via the first pressure control member 164, to enter the endoscope 116.

Figures 6A, 6B:
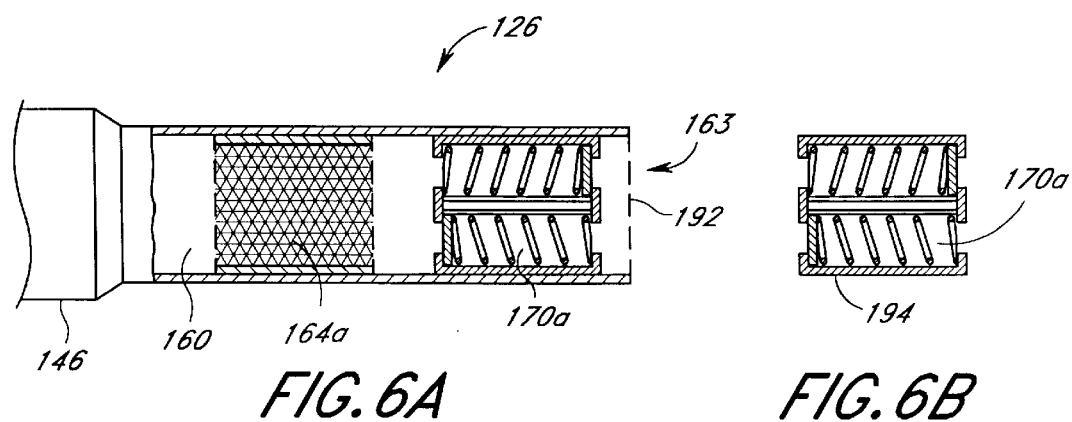
FIG. 6A is a schematic view of a third embodiment of the vent cap wherein the vent cap includes a first disposable control member, a removable control member and a breathable membrane.
FIG. 6B is a schematic view of a removable control member of the vent cap shown in FIG. 6A wherein the removable control member includes a dual valve system.

FIG. 6A shows a third embodiment of the vent cap 126 of the present invention. In this embodiment, the cap 126 may comprise the disposable first control member 164A, a disposable breathable membrane 192 and a removable second control member 170A. As shown in FIG. 6A, the disposable control member 164A may be initially sealably disposed into the housing 160. Subsequently, the removable control member 170A may be sealably placed into the housing 160. The opening 163 of the housing 160 is covered with a disposable breathable membrane 192 which can be changed after each use of the cap 126. As shown in FIG. 6B, the second pressure control member 170A can be configured as a removable component of the vent cap 126. In this respect, the second pressure control member 170A may, for example, be manufactured as a separate dual valve device having a cylindrical body 194 configured to allow insertion of the removable control member 170A into the housing 160. In this embodiment, the breathable membrane 192 prevents water from entering into the housing 160 and contacting the check valves 172 and 174.

Figure 7:
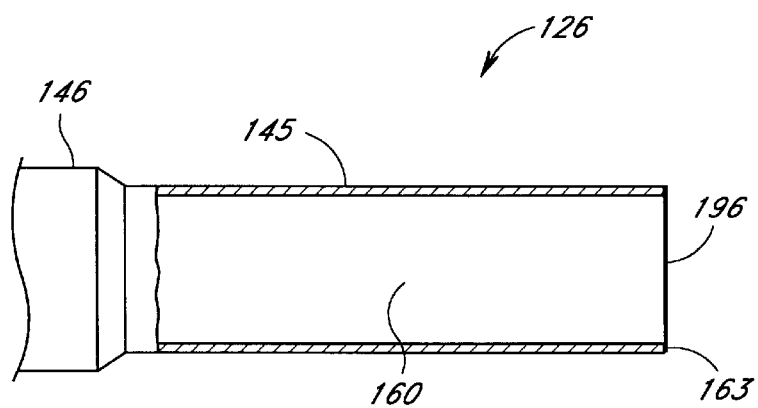
FIGS. 7–12C are schematic views of different embodiments of the vent cap.

FIG. 7 shows a fourth embodiment of the present invention. In this embodiment, the opening 163 of the cap housing 160 may be sealably covered by a non-breathable barrier 196, such as a membrane made of PP, PL, or aluminum foil. The non-breathable membrane 196 advantageously blocks the communication between the environment and the endoscope 116. Neither gas nor liquid can diffuse or flow through the cap 126 into the endoscope during the liquid treatment. However, as the pressure of the chamber 102 (See FIG. 1) is reduced, the non-breathable membrane 196 breaks and releases the pressure inside the endoscope 116.

Figure 8:
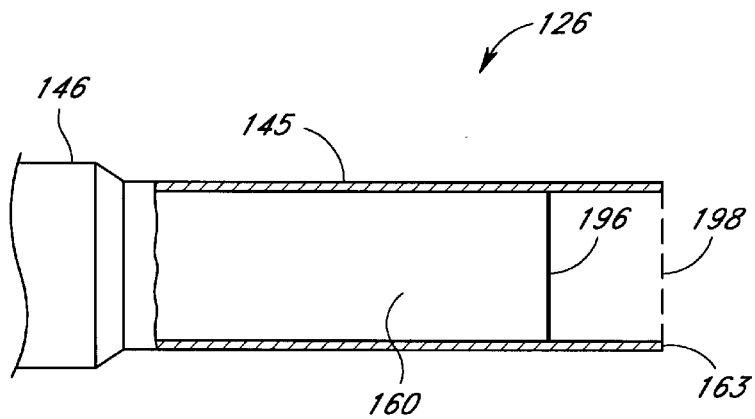

FIG. 8 shows a fifth embodiment of the present invention. In this embodiment, the breathable membrane 198 and the non-breathable membrane 196 are sealably attached to the housing 160 as in the manner shown in FIG. 8. In this embodiment, reduced pressure may break the non-breathable membrane 196, but the breathable membrane 198 is left intact on the cap 126. In this embodiment, the breathable membrane 198 advantageously prevents any residual liquid from entering into the cap 126 when the non-breathable membrane 196 breaks under reduced pressure. This embodiment is especially suitable for process sequences using atmospheric pressure cleaning and rinsing, and subsequently drying under reduced pressure.

Figure 9:
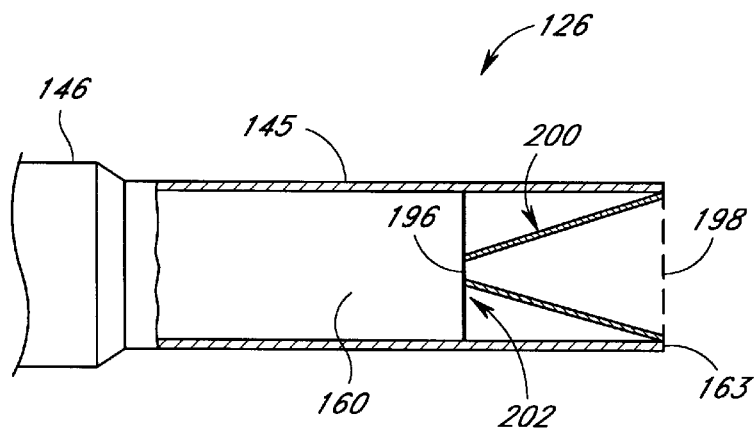

FIG. 9 shows a sixth embodiment wherein a sharp edged device 200, such as a cone shaped metal plate with a sharp tip 202 or a needle, or the like, is interposed between the non-breathable membrane 196 and the breathable membrane 198. In application, reduced pressure biases the non-breathable membrane towards the sharp tip 202 of the cone 200 so that the non-breathable membrane 196 is mechanically punctured to release the pressure inside the endoscope 116.

It will be understood that this invention is susceptible to modification in order to adapt it to different uses and conditions. The following embodiments are given for exemplary purposes and are not intended to impose limitations on the subject invention. Accordingly, FIG. 10A–10C represent three alternative embodiments produced by combining the preferred embodiment with the fourth, fifth and sixth embodiments.

Figure 10A:
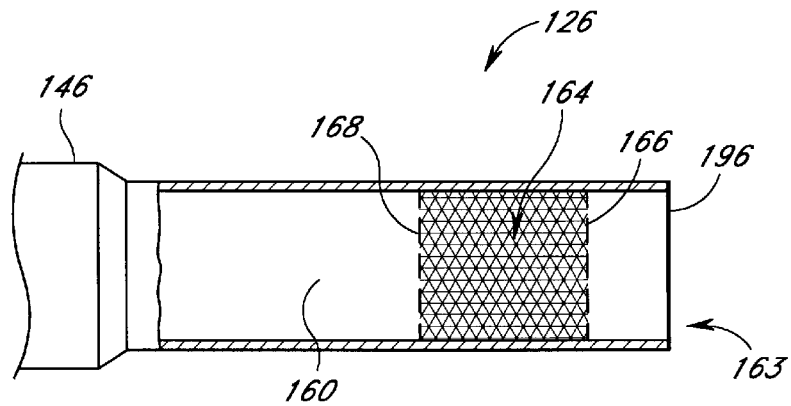

As shown in FIG. 10A, in a seventh embodiment, the vent cap 126 may comprise the first pressure control member 164 and the non-breathable membrane 196. In this embodiment, the pressure control member 196 may be positioned at an inner location within the cap housing 160 so that the cap opening 163 is sealably covered by the non-breathable membrane 196. In use, the non-breathable membrane 196 may advantageously eliminate the initial contact of moisture with the gas transmissive removal zone 165 inside the first pressure control member 164 during the liquid treatment stage. This saves the drying agents (desiccants) for the residual moisture which might exist in the chamber 102 during the subsequent low pressure cycle and thereby provides a better protection for the endoscope 116.

Figure 10B:
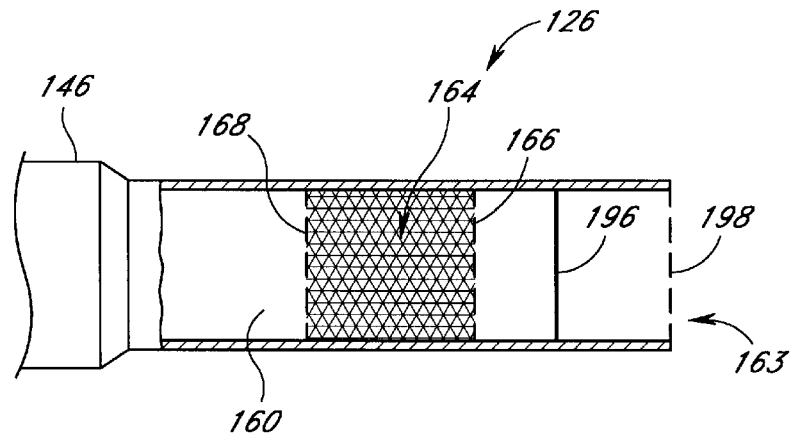

FIG. 10B shows an eighth embodiment of the present invention. As a departure from the previous embodiment, in this embodiment of the vent cap 126, the non-breathable membrane 196 is interposed between the breathable membrane 198 and the first pressure control member 164 as in the manner shown in FIG. 10B.

Figure 10C:
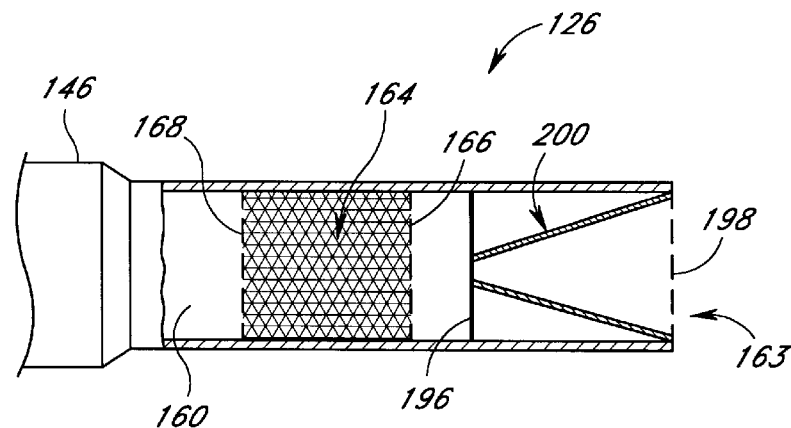

FIG. 10C shows a ninth embodiment of the vent cap 126 of the present invention. In this embodiment, the cap 126 comprises the first pressure control member 164, the non breathable membrane 196 and the breathable membrane 198, as well as the sharp edged device 200 which is interposed between the membranes 196 and 198 as in the manner shown in FIG. 10C.

Figure 11A:
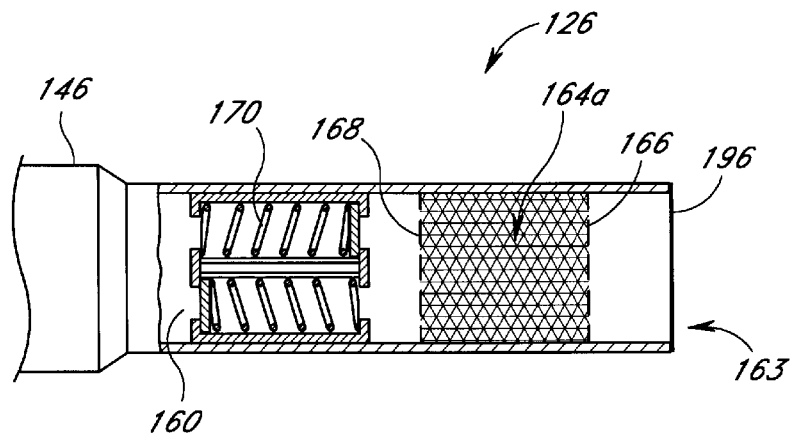
Figure 11B:
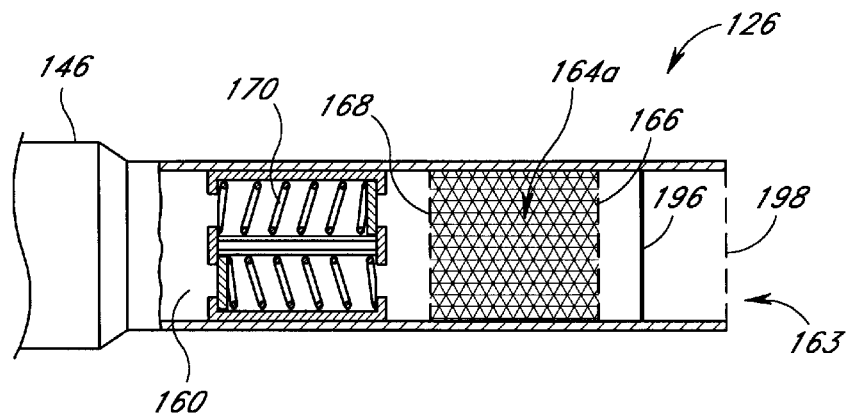
Figure 11C:
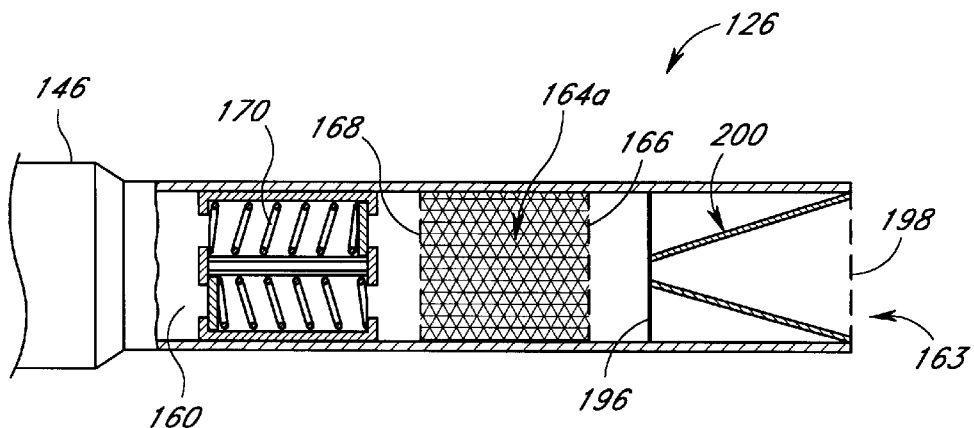

Further, FIGS. 11A–11C represent another set of embodiments produced by combining the second embodiment with the fourth, fifth, and sixth embodiments. As shown in FIG. 11A, in a tenth embodiment, the vent cap 126 may comprise the first disposable control member 164A, the second pressure control member 170 and the non-breathable membrane 196. In this embodiment, the second pressure control member 170 may be positioned at an inner position in the cap housing 160 and the non-breathable membrane 196 sealably covers the cap opening 163. The first disposable control member 164A is interposed between the non-breathable membrane 196 and the second pressure control member 170 as in the manner shown in FIG. 11A. As in the previous embodiments, the check control valves 172 and 174 in the pressure control member 170 opens and closes the cap 126 in predetermined pressure levels.

As illustrated in FIG. 11B, in an eleventh embodiment, the vent cap 126 of the present invention may be adapted to have the first disposable control member 164A, the second pressure control member 170, the non-breathable membrane 196 and the breathable membrane 198. In this embodiment, the vent cap 126 may be configured as in the manner shown in FIG. 11B.

FIG. 11C shows a twelfth embodiment of the present invention. In this embodiment, the cap 126 comprises the first disposable control member 164A, the second pressure control member 170, the non-breathable membrane 196 and the breathable membrane 198 as well as the sharp edged device 200 which is interposed between the membranes 196 and the 198 as in the manner shown in FIG. 11C.

Figure 12A:
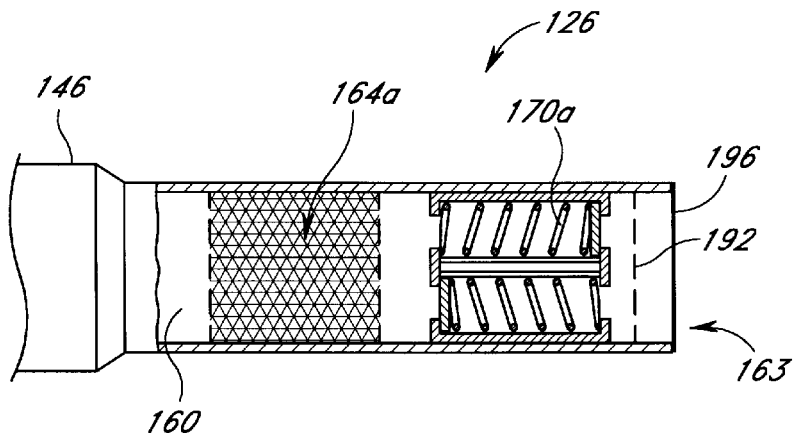
Figure 12B:
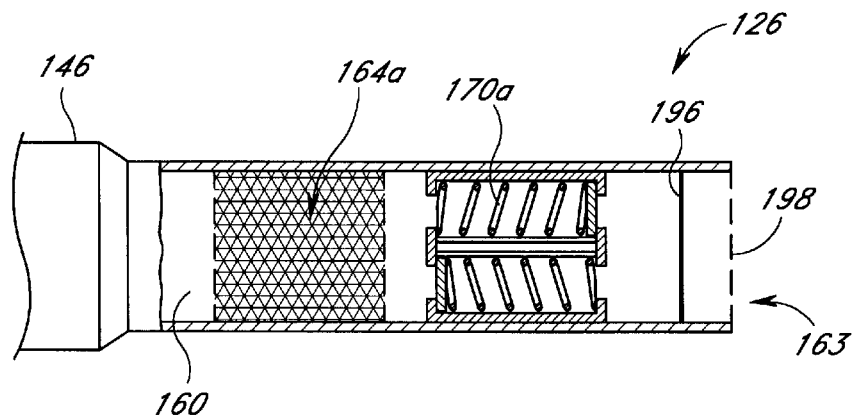
Figure 12C:
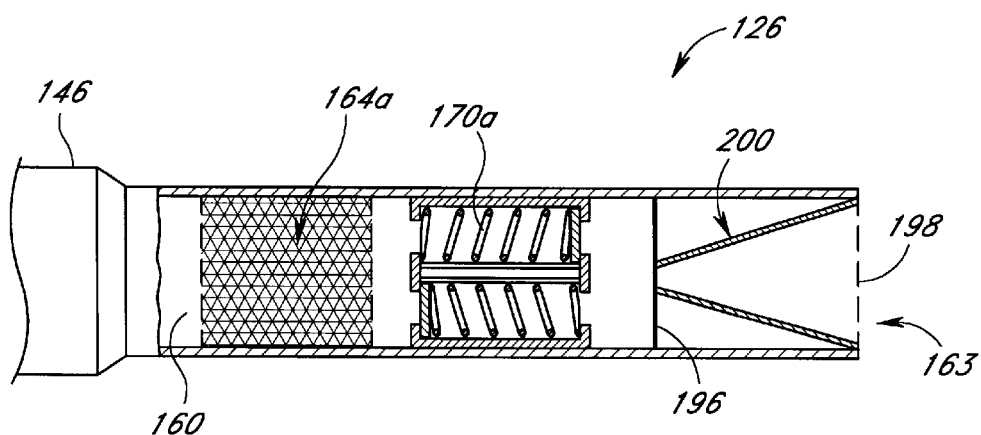

Finally, FIGS. 12A–12C represent a final set of embodiments produced by combining the third embodiment with the fourth, fifth and the sixth embodiment. As shown in FIG. 12A, in a thirteenth embodiment, the vent cap 126 may comprise the first disposable control member 164A, the second removable control member 170A, the disposable breathable membrane 192 and the non-breathable membrane 196. In this embodiment, the second removable control member 170A may be interposed between the disposable breathable membrane 192 and the first disposable control member 164A which is positioned at an inner position in the cap housing 160. The non-breathable membrane 196 sealably covers the cap opening 163.

FIG. 12B shows a fourteenth embodiment of the present invention. In this embodiment, the cap 126 comprises the first disposable control member 164A, the second removable control member 170A, the non-breathable membrane 196 and the breathable membrane 198 which sealably covers the opening 163 of the cap 126. As a departure from the previous embodiment, in this embodiment of the vent cap 126, the non-breathable membrane 196 is interposed between the breathable membrane 198 and the second removable control member 170A as in the manner shown in FIG. 12B.

FIG. 12C shows a fifteenth embodiment of the vent cap 126 of the present invention. In this embodiment, the cap 126 comprises the first disposable control member 164A, the second removable control member 170A, the non-breathable membrane 196 and the breathable membrane 198 as well as the sharp edged device 200 which is interposed between the membranes 196 and 198 as in the manner shown in FIG. 12C.

As described above, various embodiments of the present invention allow the pressure to equalize between the internal space of the endoscope 116 and the environment surrounding the endoscope's sheath 122, while reducing the flow of any liquid, water vapor and hydrogen peroxide into the endoscope's internal space. As also described above, other embodiments of the present invention utilize a non-breathable membrane 196 to block the fluid communication between the internal space of the endoscope 116 and the environment surrounding the endoscope 116. However, as the pressure of the environment is reduced, the non-breathable membrane 196 breaks open thereby equalizing the pressure between the internal space of the endoscope and the environment surrounding the endoscope 116. Therefore, the present invention allows both atmospheric pressure liquid phase cleaning and/or sterilization and subsequent reduced pressure drying and/or sterilization of endoscopes in a continuous fashion.

In fact, the application of the vent cap 126 of the present invention is not limited to the above described processes. The present invention is particularly advantageous over conventional EtO caps (ethylene oxide caps) and may replace them. EtO caps can be either open or closed, which prevents their use during a continuous liquid pretreatment and subsequent reduced pressure treatment. As explained above, the vent cap 126 of the present invention opens the port but does not allow the flow of liquid into the endoscope. Therefore, the vent cap 126 can advantageously be used regardless of the endoscope type and the sterilization process.

Hence, although the foregoing description of the preferred embodiment of the present invention has shown, described and pointed out the fundamental novel features of the invention, it will be understood that various omissions, substitutions, and changes in the form of the detail of the apparatus and method as illustrated as well as the uses thereof, may be made by those skilled in the art, without departing from the spirit of the present invention. Consequently, the scope of the present invention should be defined by the appended claims.

What is claimed is:

1. A device for use with an endoscope that allows the equalization of the pressure between an internal space of the endoscope and an environment outside the endoscope, the device comprising:

a housing that is adapted to receive a port that is connected to an internal space of the endoscope, wherein said housing defines an opening;

a gas-transmissive removal zone in said opening, said removal zone comprising a desiccant material and a material which removes an antimicrobial agent; and at least one hydrophobic breathable membrane between said removal zone and said environment.

2. The device of claim 1, wherein said material is a catalyst which decomposes said antimicrobial agent.

3. The device of claim 1, wherein said material is an absorbent which absorbs said antimicrobial agent.

4. The device of claim 2, wherein said desiccant material and said catalyst are between said hydrophobic breathable membrane and a gas permeable membrane.

5. The device of claim 1, wherein said hydrophobic breathable membrane comprises porous PTFE or porous polyolefin.

6. The device of claim 1, wherein said desiccant comprises a material selected from the group consisting of $P_2O_5$, $BaO$, $CaO$ or $Al_2O_3$ and mixtures thereof.

7. The device of claim 1, further comprising a dual valve system which is positioned in said opening wherein said dual valve system comprises an inlet check valve and an outlet check valve.

8. The device of claim 1, wherein said device is placed into a system comprising a pump to reduce pressure in said environment.

9. A method for equalizing pressure within an internal space of an endoscope with a pressure in an environment outside the endoscope, said endoscope having a port that is connected to said internal space, the method comprising the steps of:

placing the endpscope within a chamber;

connecting 5a pressure control device to the port, said pressure control device having a housing that defines an opening and a gas transmissive removal zone positioned within said opening, wherein the placing and connecting steps can be performed in either order;

subjecting the endoscope to a liquid phase environment at a first pressure, while said removal zone reduces entry of the liquid into the internal space of the endoscope through said opening; and subjecting the endoscope to a subsequent gas phase environment comprising water vapor and gaseous antimicrobial agent at a second pressure less than the first pressure thereby inducing a phase change of at least some of said liquid to a gas, wherein said removal zone absorbs said water vapor and removes said antimicrobial agent and permits at least some air within the internal space of the endoscope to escape to the environment through said opening.

10. The method of claim 9, wherein the first subjecting step comprises subjecting the endoscope to a cleaning solution comprising water and a cleaning detergent or to a sterilizing solution comprising water and antimicrobial agent.

11. The method of claim 9, wherein said antimicrobial agent is $H_2O_2$.

12. The method of claim 9, wherein a dual valve opens to permit gas exchange between the internal space of the endoscope and the environment.

13. The method of claim 12, wherein said valve opens at a pressure differential of about 5 to 270 Torr.

14. The method of claim 9, wherein the second subjecting step comprises a reduced pressure drying process or a reduced pressure sterilization process.

15. A device for use with an endoscope that allows the equalization of the pressure between an internal space of the endoscope and an environment, the device comprising:

a housing that is adapted to receive the port that is connected to an internal space of the endoscope, wherein said housing defines an opening;

a membrane sealing said opening, wherein said membrane is gas and liquid impermeable and breaks when a reduced pressure is applied; and a sharp-edged device adapted to puncture said membrane when the reduced pressure is applied.

16. The device of claim 15, wherein said membrane comprises a non-breathable membrane which is made of polyethylene, polypropylene or aluminum foil.

17. The device of claim 15, additionally comprising a hydrophobic, gas-permeable membrane between the environment and the impermeable membrane.

18. The device of claim 15, further comprising a gas transmissive removal zone positioned in said opening wherein said removal zone is comprised of a mixture of a desiccant and a material which removes an antimicrobial agent.

19. The device of claim 18, wherein said desiccant comprises a material selected from the group consisting of $P_2O_5$, BaO, CaO or $Al_2O_3$ and mixtures thereof.

20. The device of claim 18, wherein said material comprises a metallic catalyst.

21. The device of claim 18, further comprising a dual valve assembly positioned in said opening wherein said dual valve assembly comprises an outlet check valve and an inlet check valve.

22. The device of claim 15, wherein said device is placed into a system comprising a pump to reduce pressure in said environment.

23. A method for equalizing pressure within an internal space of an endoscope with a pressure in an environment outside the endoscope, said endoscope having a port that is connected to said internal space, the method comprising the steps of:

placing the endoscope within a chamber;

connecting an adaptor to said port, said adaptor having a housing that defines an opening with a non-permeable membrane sealing said opening, wherein the placing or connecting steps can be performed in either order;

subjecting the endoscope to a liquid at a first pressure, said membrane preventing transmission of gas and liquid between the internal space of the endoscope and the environment outside the endoscope through said opening; and subjecting the endoscope to a subsequent gas phase environment at a second pressure lower than the first pressure wherein said membrane breaks upon application of the reduced pressure and permits gas within the internal space of the endoscope to escape to the environment through said opening.

24. The method of claim 23, wherein the first subjecting step comprises subjecting the endoscope to a cleaning solution comprising water and a cleaning detergent or a sterilizing solution comprising water and antimicrobial agent.

25. The method of claim 23, wherein the second subjecting step comprises a reduced-pressure drying process or reduced-pressure sterilization process.

26. The method of claim 23, wherein the pressure difference between the second pressure and the pressure in said internal space is about 5 to about 270 Torr when said membrane breaks.

27. The method of claim 23, wherein said membrane breaks by being punctured by a sharp-edged device.

28. The method of claim 23, wherein said environment comprises water vapor and an antimicrobial agent, said method additionally comprising:

removing said water vapor; and removing said antimicrobial agent from any gas entering from said environment toward said internal space of said endoscope.

29. The method of claim 23, wherein said water is removed by being absorbed by an absorbent material.

30. The method of claim 23, wherein a dual valve opens after said membrane breaks.

* * * * *

UNITED STATES PATENT AND TRADEMARK OFFICE
CERTIFICATE OF CORRECTION

PATENT NO.    : 5,868,667
DATED         : February 9, 1999
INVENTOR(S)   : Szu-Min Lin et al.

It is certified that error appears in the above-identified patent and that said Letters Patent is hereby corrected as shown below:

Column 12, claim 9,
Line 23, replace "5a" with -- a --.

Signed and Sealed this

Twenty-sixth Day of March, 2002

Attest:

Attesting Officer

JAMES E. ROGAN
Director of the United States Patent and Trademark Office